United States Patent [19]

Lohn

[11] 4,225,308

[45] Sep. 30, 1980

[54] PNEUMATIC LAMINAR MOTOR FOR DENTAL USE

[75] Inventor: Gerd Lohn, Biberach, Fed. Rep. of Germany

[73] Assignee: Kaltenbach & Voigt GmbH & Co., Biberach an der Riss, Fed. Rep. of Germany

[21] Appl. No.: 39,331

[22] Filed: May 15, 1979

[30] Foreign Application Priority Data

May 17, 1978 [DE] Fed. Rep. of Germany ....... 2821560

[51] Int. Cl.³ .............................................. A61C 1/05
[52] U.S. Cl. ................................... 433/132; 433/115; 418/173
[58] Field of Search ................ 433/132, 115; 415/503; 418/173, 16; 308/9

[56] References Cited

U.S. PATENT DOCUMENTS

| | | | |
|---|---|---|---|
| 2,575,524 | 11/1951 | Mitchell | 418/270 |
| 2,590,132 | 3/1952 | Scognamillo | 418/173 |
| 2,590,729 | 3/1952 | Scognamillo | 418/173 |
| 3,309,965 | 3/1967 | Weickgenannt | 433/132 |
| 3,582,243 | 6/1971 | Rhine | 418/173 |
| 4,120,623 | 10/1978 | Lohn | 433/132 |
| 4,177,024 | 12/1979 | Lohn | 418/173 |

Primary Examiner—Robert Peshock
Assistant Examiner—John J. Wilson
Attorney, Agent, or Firm—Haseltine, Lake & Waters

[57] ABSTRACT

A pneumatic laminar motor, for dental purposes, having a sleeve-like housing forming the stator with circular cylindrical inside wall and a rotor inside touching that wall. The rotor has a diameter smaller than the inside wall and its rotary axis is parallel to, but displaced from the axis of the inside wall. The lengthwise slots of the rotor has radially movable lamellas with their outer ends pointing to the inside wall. An air inlet opening from the air supply conduit and an air outlet opening discharge into the space between rotor and inside wall. A freely rotating bearing ring is located between the inside wall and the outer ends of the lamellas and is coaxial with the inside wall. The outer ends of the lamellas contact the bearing ring. Compressed air enters through the air inlet opening into the space between rotor and inside wall and pushes the nearest lamella ahead of it to turn the motor. The bearing ring is divided into two bearing ring sections with an annular space between them, with the rotor being fastened rotation-proof to the bearing ring sections. The air inlet opening discharges into the annular space.

9 Claims, 4 Drawing Figures

PNEUMATIC LAMINAR MOTOR FOR DENTAL USE

BACKGROUND OF THE INVENTION

The present invention related to a pneumatic laminar motor, for dental purposes, consisting of a sleeve-like housing forming the stator, with circular cylindrical inside wall and a rotor arranged within and contacting this inside wall. This rotor has a diameter smaller than the inside wall of the circular cylinder and its axis of rotation runs parallel to the axis of the inside wall of the circular cylinder and is displaced from it. The lengthwise slots of the rotor has radially movable lamellas with their outer ends pointing to the circular cylindrical inside wall. An air inlet opening for the compressed air, coming from a compressed air supply conduit, and an air outlet opening discharge into the space between rotor and circular cylindrical inside wall. Between the circular cylindrical inside wall and the outer ends of the lamellas there is located a bearing ring which is freely rotatable relative to the inside wall and which is coaxial with the inside wall. The outer ends of the lamellas contact the bearing ring. When compressed air is applied to the motor, it enters through the air inlet openings(s) into the space between rotor and circular cylindrical inside wall and pushes the nearest lamella protruding furtherest from the rotor ahead of it so that the rotor starts to turn and the next lamella is charged by the compressed air. The speed of the laminar motor may run between 20,000 and 100,000 rpm. The outer lamella ends contact the freely rotatable bearing ring and are to be protected in this manner against any sliding friction the bearing ring participates in the rotation of the rotor due to static friction of the outer lamella ends at the inside of the bearing ring.

Such a laminar (or lamellar) motor is known from the German Laid-Open Document No. 26 21 486. The air inlet opening(s) in this known laminar motor discharge axially, i.e., from one motor face side into the space between rotor and circular cylindrical inside wall. Therefore, the location of the compressed air inlet conduit up to this radial entry is relatively complicated. Not only because of this axial discharge by itself, but also because of the small dimensions of the laminar motor required for dental handpieces, the throughflow of air per unit of time is relatively low so that difficulties arise when starting the motor. On the other hand it has been found that the desired rotation participation of the bearing ring caused by the outer lamella ends does not always take place, even though the inside wall of the bearing ring of this known laminar motor has axial grooves of a flat curved cross section to receive the outer ends of the lamellas. Because of the flatness of the grooves and the troubles and impediments caused by the aforementioned difficulties during the buildup of an air cushion between bearing and circular cylindrical housing inside wall and because of a restriction of the free rotation of the bearing ring, the lamella ends slide out of the grooves during certain operation modes and/or shift or bend such that the performance of the motor deteriorates appreciably.

SUMMARY OF THE INVENTION

The present invention provides a laminar motor of the above type by ensuring a sufficiently large flow quantity of air per unit of time and avoiding the hazard of shifting or deforming the lamellas.

The advantages achieved by the invention are that subdividing the bearing ring and the discharge of the air inlet opening into the annular space allow direct air application to the motor and increase the efficiency of the motor such that enough air flow per unit of time is available for a satisfactory operation. In spite of the increased power of the motor, a shifting or deformation of the lamellas is prevented by the rigid connection of the rotor to the bearing ring.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
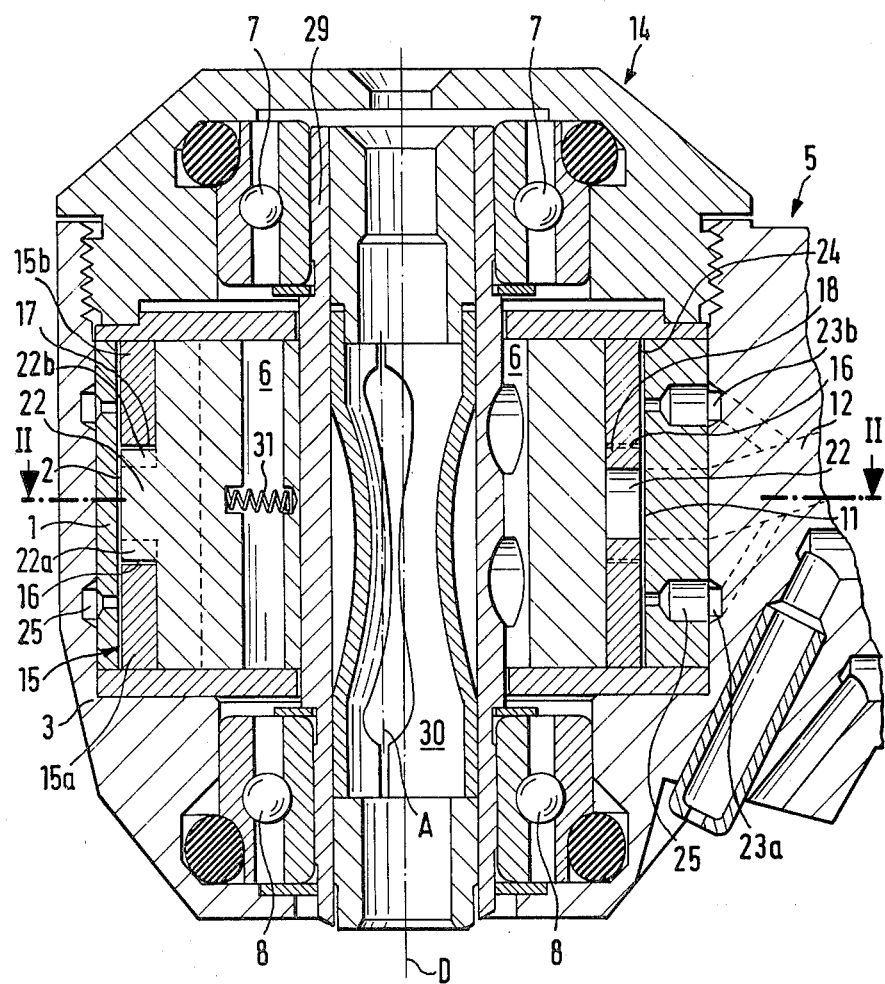
FIG. 1 shows a section through a pneumatic laminar motor installed in the angled head of a dental handpiece.

The pneumatic laminar motor consists of a sleeve-like housing 1 forming the stator, with circular cylindrical inside wall 2. The housing 1 may be enclosed by an outer jacket 3 which forms the head housing of the angled head 4 of a dental handpiece 5. Inside the housing is a rotor 6 of circular cross section mounted in bearings 7, 8 arranged on the face sides. The rotor 6 contacts the inside wall 2 of the housing 1 constituting the stator, and has a diameter smaller than the inside wall 2. The rotary axis D of rotor 6 is parallel to the axis A of the circular cylindrical inside wall of the housing 1 forming the stator and is displaced from it. In lengthwise slots 9 of rotor 6, lamellas 10 are located with their outer ends facing the circular cylindrical inside wall 2, so as to be movable radially. An air inlet opening 11 for compressed air coming from a compressed air supply conduit 12, and an air outlet opening discharge into the space between rotor 6 and circular cylindrical inside wall 2. The air outlet opening 13 is connected to an exhaust air duct 14. Between the circular cylindrical inside wall 2 of the housing 1 forming the stator and outer end of the lamellas 10 is a bearing ring 15 which is freely rotatable relative to the inside wall 2 and is coaxial with the inside wall. The bearing ring is in contact with the outer ends of the lamellas.

The bearing ring 15 is cut transversely, forming two bearing ring sections 15a, 15b(FIG. 1). The two bearing ring sections 15a, 15b are arranged next to each other, leaving an annular space 16. The rotor 6 is connected to the bearing ring sections 15a, 15b to prevent relative rotation. The air inlet opening 11 discharges into the annular space 16.

The ring face surfaces 17 of the bearing ring sections 15a, 15b have indentations 18 with radial lateral walls 19, 20 for receiving radial projections of rotor 6 to assure rotation-proof connection. The indentations 18 may also be open towards the ring exterior, and in that case would completely penetrate the wall thickness of the bearing ring sections.

Figure 3:
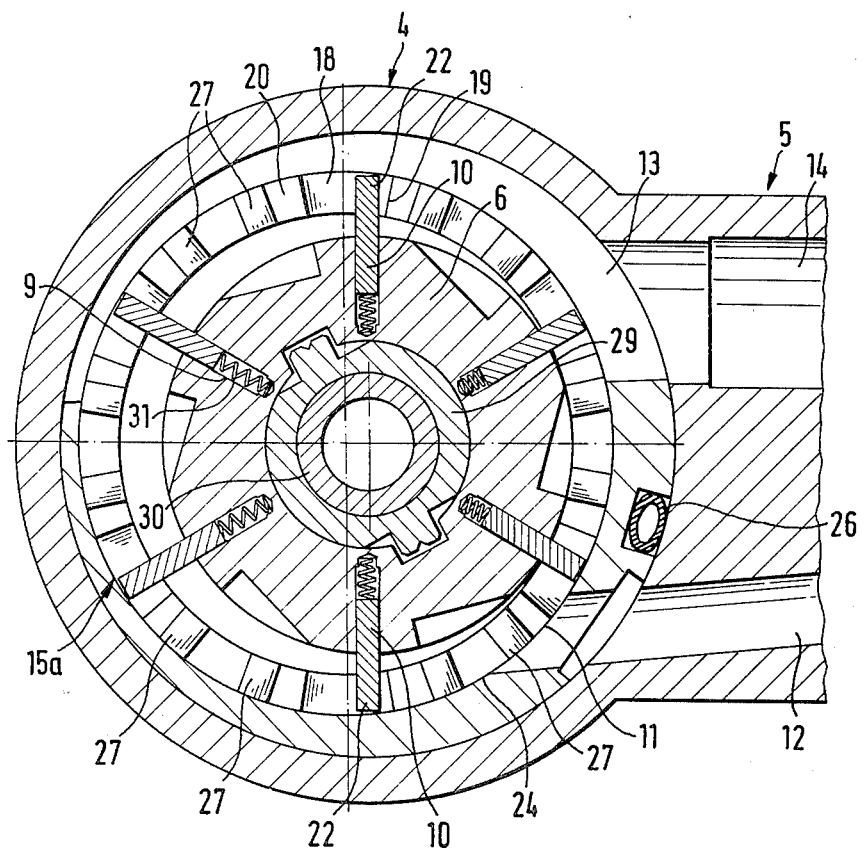
FIG. 3 shows an embodiment different from that of FIG. 2.
Figure 4:
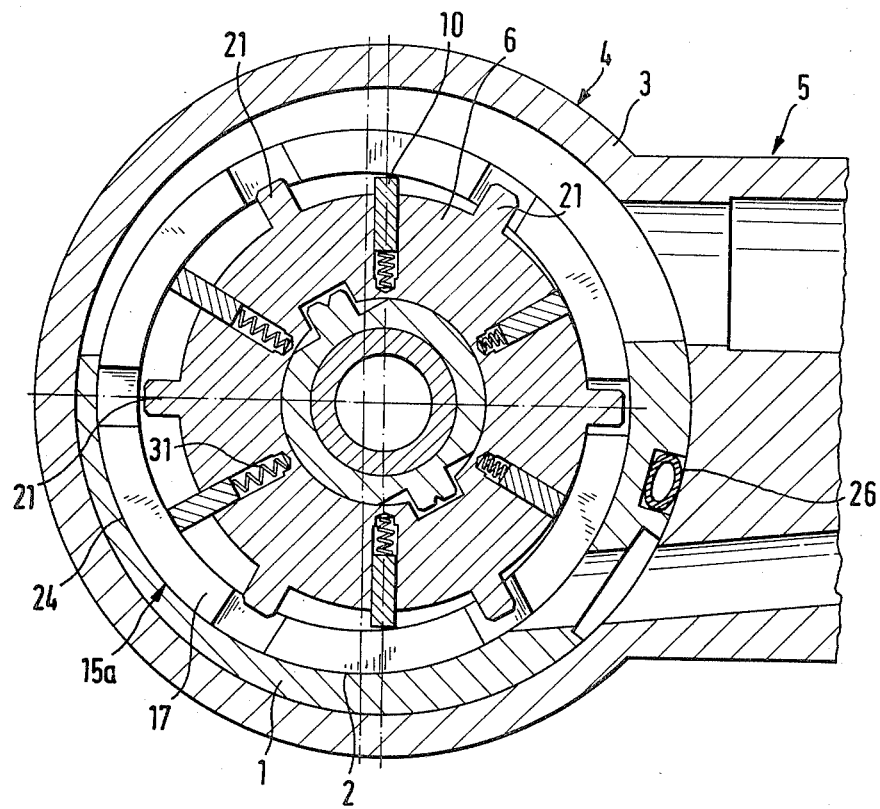
FIG. 4 shows another modified embodiment.

The mentioned radial projections of the rotor 6 may be formed according to the embodiment of FIG. 4 by projections 21 rigidly arranged on the periphery of the rotor 6. In another embodiment according to FIGS. 1 to 3, the radial projections are formed by continuations 22 arranged on the outer ends of the lamellas 10. These continuations engage indentations 18.

Figure 2:
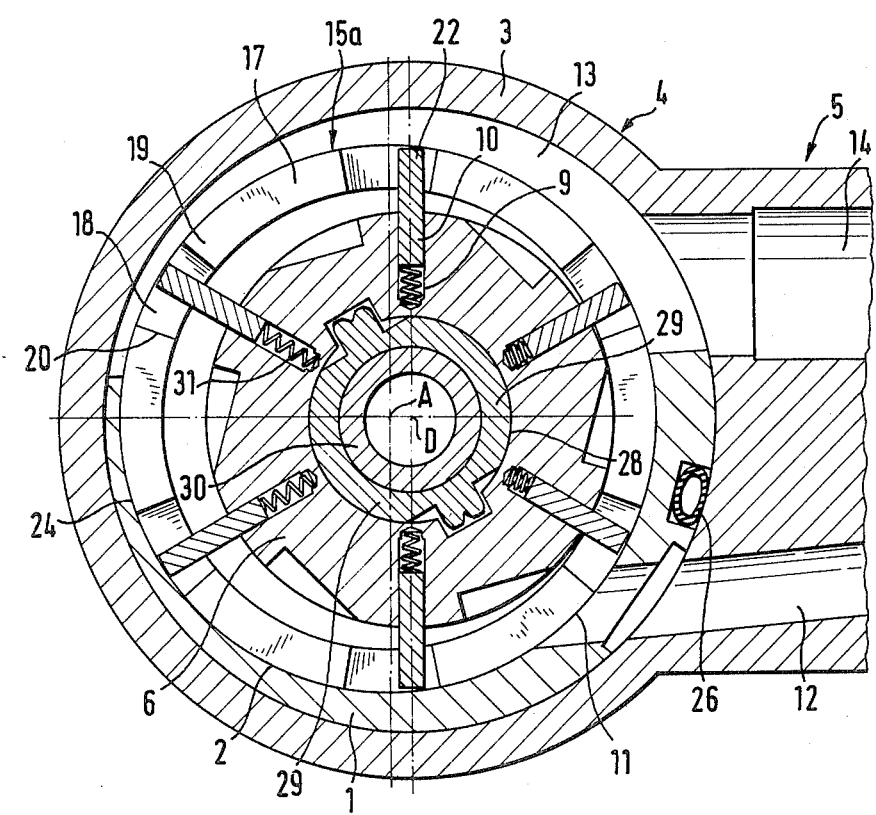
FIG. 2 shows a section taken along line II—II in FIG. 1.

As shown in FIGS. 2 to 4, the indentations 18 and the radial projections 21 or 22 are distributed uniformly over the periphery of the bearing ring sections 15a, 15b or of rotor 6.

As evident from the left-hand of FIG. 1, the radial projections 21 and 22, respectively, have an axial length such that they engage with one end 22a the indentation 18 of one bearing 15a from the space 16 between the bearing ring sections 15a, 15b, and with their other end 22b engage the indentation 18 of the other bearing ring section.

According to FIG. 1, the housing 1 forming the stator has for every bearing ring section 15a, 15b an annular channel 23a, 23b connected to the compressed air supply conduit 12, 12 leading to the air inlet opening 11. Air passages 25 issue from this annular channel into an annular gap 24 located between bearing ring section 15a or 15b and the circular cylindrical wall 2 of housing 1. By supplying the annular gap 24 with compressed air, an air cushion is built up for the associated bearing ring section 15a or 15b.

As shown in FIGS. 2 to 4, the compressed air supply conduit 12 or the air inlet opening 11, respectively, is sealed form the air outlet opening 13 by means of a strip-like or hose-like seal 26 located between the housing 1 and the outer jacket 3.

In the embodiment of FIG. 3, turbine-blade-like shapes 27 are arranged at the ring face surfaces 17 of the bearing ring sections 15a, 15b. These shapes assist the drive, especially when starting the laminar motor.

The rotor 6 has a central axial cavity 28 in which a hollow shaft 29 is arranged and connected to it in a rotation-proof manner. The hollow shaft 29 has a collet 30 which receives a dental tool (not shown), and is connected, together with the tool, in a rotation proof manner to the hollow shaft 29 and to the rotor 6.

The construction of the laminar motor with the compressed air supplied jet-like in the center of the lamellas with respect to the rotor axis ensures the immediate buildup of a dynamic air cushion when starting the laminar motor, with the participation of the bearing ring 15 in the rotation by the described rotation-proof connection between the rotor 6 and the bearing ring sections 15a, 15b being ensured.

The lamellas 10 with their outer ends are either under the action of the centrifugal force—during the rotation of rotor 6—or under the action of compression springs 31 arranged in the lengthwise slot 9 of rotor 6 (FIG. 3).

Without further anaylsis, the foregoing will so fully reveal the gist of the present invention that others can, by applying current knowledge, readily adapt it for various applications without omitting features that, from the standpoint of prior art, fairly constitute essential characteristics of the generic or specific aspects of this invention, and therefore, such adaptations should and are intended to be comprehended within the meaning and range of equivalence of the following claims.

What is claimed is:

1. A pneumatic laminar motor for dental use comprising: a sleeve-shaped housing operating as stator, said housing having a circular cylindrical inside wall; a circular cylindrical rotor inside said inside wall and contacting said inside wall, said rotor having a diameter smaller than said circular cylindrical inside wall and a rotary axis; said circular cylindrical inside wall having an axis parallel to and displaced from said rotary axis; radially movable lamellas located in lengthwise slots of said rotor, said lamellas having outer ends facing said circular cylindrical wall; at least one air inlet opening for compressed air coming from a compressed air supply conduit; at least one air outlet opening discharging into a space between said rotor and said circular cylindrical inside wall; a bearing ring freely rotatable relative to and coaxial with said circular cylindrical inside wall, said bearing ring being located between said circular cylindrical inside wall and said outer ends of said lamellas contacting said bearing ring, said bearing being divided transversely forming at least two bearing ring sections, said bearing rings being arranged next to each other leaving an annular space in between, said rotor being connected rotation-proof to said bearing ring sections; said air inlet opening discharging into said annular space.

2. A laminar motor as defined in claim 1 including facing ring face surfaces of said bearing ring sections having indentations open towards an interior side of said bearing ring; radial lateral boundary walls for receiving radial projections of said rotor.

3. A laminar motor as defined in claim 2 wherein said radial projections are formed by elevations rigidly attached to the periphery of said rotor.

4. A laminar motor as defined in claim 2 wherein said radial projections are formed by continuations at said outer ends of said radially movable lamellas.

5. A laminar motor as defined in claim 2 wherein said indentations and said radial projections are distributed uniformly over the periphery of said bearing ring sections and of said rotor.

6. A laminar motor as defined in claim 2 wherein said radial projections have an axial length such that one end engages one of said indentations of one of said bearing sections and another end engages one of said indentations of the other of said bearing ring sections, and said air inlet opening discharges into said annular space.

7. A laminar motor as defined in claim 2 including turbine-blade means on said facing ring face surfaces of said bearing ring sections.

8. A laminar motor as defined in claim 1 including annular channels associated with each of said bearing ring sections in said housing, said annular channels being connected to said compressed air supply conduit leading to said air inlet opening; air passage discharging into an annular gap between said bearing ring sections and said circular cylindrical walls.

9. A laminar motor as defined in claim 1 including a seal for sealing said air inlet opening against said air outlet opening, an outer jacket enclosing said housing; said seal being located between said housing and said outer jacket.

* * * * *